United States Patent
Chang

(10) Patent No.: US 10,251,367 B2
(45) Date of Patent: Apr. 9, 2019

(54) ENVIRONMENT CLEANING SYSTEM FOR AN ANIMAL BREEDING HOUSE

(71) Applicant: Chia-Ming Chang, Taichung (TW)

(72) Inventor: Chia-Ming Chang, Taichung (TW)

(*) Notice: Subject to any disclaimer, the term of this patent is extended or adjusted under 35 U.S.C. 154(b) by 435 days.

(21) Appl. No.: 15/250,353

(22) Filed: Aug. 29, 2016

(65) Prior Publication Data
US 2017/0105383 A1    Apr. 20, 2017

(30) Foreign Application Priority Data

Oct. 16, 2015  (TW) ............................. 104133995 A

(51) Int. Cl.
| | |
|---|---|
| *A01K 1/00* | (2006.01) |
| *A61L 9/00* | (2006.01) |
| *B01D 46/00* | (2006.01) |
| *B01D 46/44* | (2006.01) |
| *A61L 9/14* | (2006.01) |

(52) U.S. Cl.
CPC .............. *A01K 1/0047* (2013.01); *A61L 9/00* (2013.01); *A61L 9/145* (2013.01); *B01D 46/0027* (2013.01); *B01D 46/44* (2013.01); *B01D 46/448* (2013.01); *A61L 2209/14* (2013.01); *A61L 2209/22* (2013.01); *B01D 2279/40* (2013.01)

(58) Field of Classification Search
CPC .... A01K 1/0047; A01K 1/0052; A01K 31/18; A01K 31/20
See application file for complete search history.

(56) References Cited

U.S. PATENT DOCUMENTS

| | | | | |
|---|---|---|---|---|
| 6,321,687 B1* | 11/2001 | Lemmon | ............... | A01K 1/0047 119/448 |
| 2006/0118058 A1* | 6/2006 | Moore, Jr. | ........... | A01K 1/0047 119/448 |
| 2006/0249093 A1* | 11/2006 | Fuksa | .................. | A01K 1/0047 119/482 |
| 2011/0061601 A1* | 3/2011 | Correa | ................. | A01K 1/0029 119/437 |

FOREIGN PATENT DOCUMENTS

| | | |
|---|---|---|
| CN | 101524051 A | 9/2009 |
| TW | M518756 U | 3/2016 |

* cited by examiner

*Primary Examiner* — Monica L Williams
(74) *Attorney, Agent, or Firm* — C. G. Mersereau; DeWitt LLP

(57) ABSTRACT

An environment cleaning system for an animal breeding house has an outside environment, a breeding house, an air covering, and a cleaning device. The breeding house is deposited in the outside environment. The air covering is deposited in the outside environment and is mounted around the breeding house. The air covering is used to buffer the air pressure between the outside environment and the breeding house. The cleaning device is deposited in the outside environment, is connected to the air covering and the breeding house, and has an air exchanging unit and at least one filtering unit. The air exchanging unit controls the relative pressure among the outside environment, the air covering, and the breeding house to provide a unidirectional air flowing effect, and the flowing direction of the air is based on the relative pressure between the breeding house and the air covering.

16 Claims, 6 Drawing Sheets

ENVIRONMENT CLEANING SYSTEM FOR AN ANIMAL BREEDING HOUSE

BACKGROUND OF THE INVENTION

1. Field of the Invention

The present invention relates to an environment cleaning system, and more particularly to an environment cleaning system for an animal breeding house that may provide a unidirectional flowing effect to the animal breeding house and may reach an epidemic prevention effect.

2. Description of Related Art

A conventional animal breeding house system has a breeding house and a water curtain device. The water curtain is deposited on an outer side of the breeding house to isolate the air inside from air outside the breeding house, and this may provide a protecting effect to the bred animals. Furthermore, the water curtain device has a storage tank, a pumping assembly, a watershed site, and a reflux site. The pumping assembly is used to pump water from the storage tank, and the water is discharged at the watershed site. Then, the water naturally flows to the reflux site and is recycled back to the storage tank. When the water flows down the reflux site, the water may form a water curtain to isolate the air inside from air outside the breeding house. Then, the water curtain may provide a dust-proof and filtering effect to the air outside the breeding house when the air flows into the breeding house.

However, the water curtain device of the conventional animal breeding house system cannot completely isolate the dust outside the breeding house, and the dust that is shut down by the water curtain may be moved back to the storage tank via the reflux site. When the animal epidemic situation occurs, the epidemic will be spread since the water curtain of the conventional animal breeding house system cannot provide a complete isolation effect to the breeding house.

To overcome the shortcomings, the present invention provides an environment cleaning system for an animal breeding house to mitigate or obviate the aforementioned problems.

SUMMARY OF THE INVENTION

The main objective of the present invention is to provide an environment cleaning system for an animal breeding house that may provide a unidirectional air flowing effect to the animal breeding house and may reach an epidemic prevention effect.

The environment cleaning system for an animal breeding house in accordance with the present invention has an outside environment, a breeding house, an air covering, and a cleaning device. The breeding house is deposited in the outside environment and has an inner closed space. The air covering is deposited in the outside environment, is mounted around the breeding house, and has an outer closed space between the breeding house and the air covering. The air covering is used to buffer the air pressure between the outside environment and the breeding house. The cleaning device is deposited in the outside environment, is connected to the air covering and the breeding house, and has an air exchanging unit and at least one filtering unit. The air exchanging unit may control the relative pressure among the outside environment, the air covering, and the breeding house to provide a unidirectional air flowing effect, and the flowing direction of the air is based on the relative pressure between the breeding house and the air covering.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
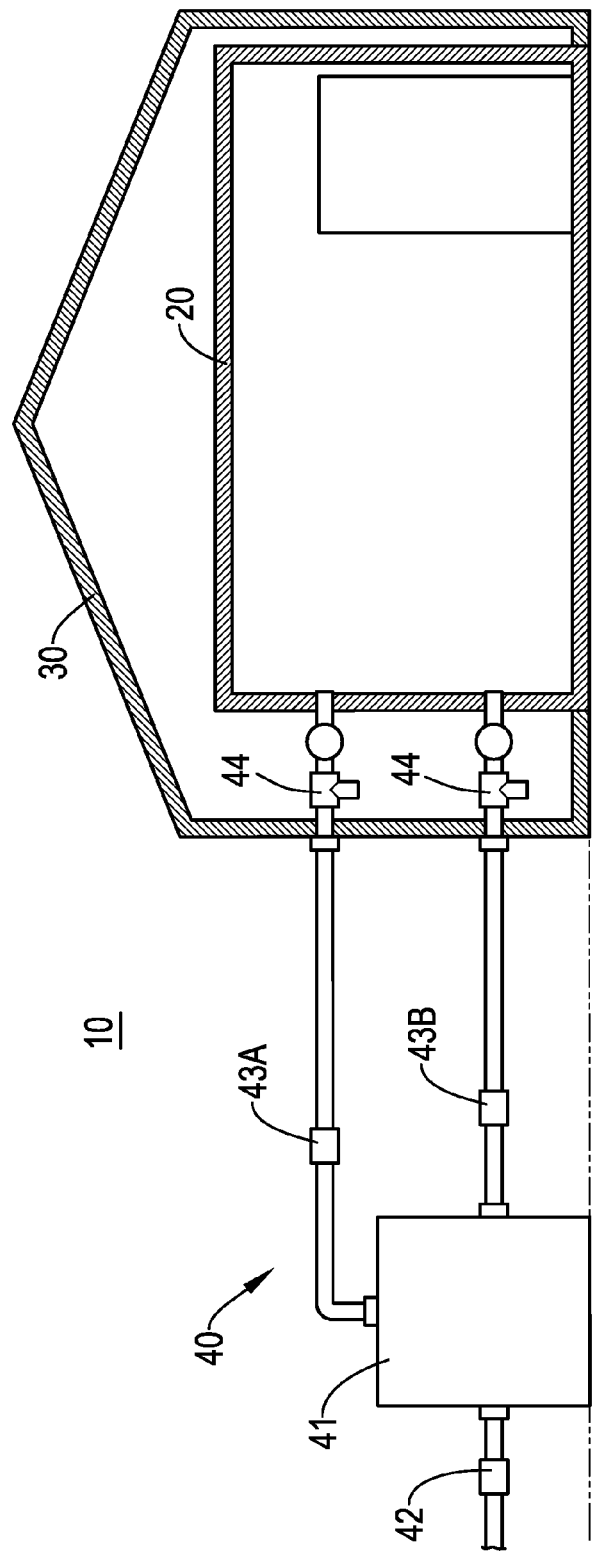
FIG. 1 is a side view in partial section of a first embodiment of an environment cleaning system for an animal breeding house in accordance with the present invention.

With reference to FIG. 1, a first embodiment of an environment cleaning system for an animal breeding house in accordance with the present invention comprises an outside environment 10, a breeding house 20, an air covering 30, and a cleaning device 40.

The breeding house 20 is deposited in the outside environment 10 and has an inner closed space. The air covering 30 is deposited in the outside environment 10, is mounted around the breeding house 20, and has an outer closed space between the breeding house 20 and the air covering 30. The air covering 30 is used to buffer the air pressure between the outside environment 10 and the breeding house 20.

The cleaning device 40 is deposited in the outside environment 10, is connected to the air covering 30 and the breeding house 20, and has an air exchanging unit 41, a sterilizing unit 42, and two filtering units 43A, 43B. The air exchanging unit 41 is deposited in the outside environment 10, is connected to the air covering 30 and the breeding house 20, and is used to exchange air among the outside environment 10, the air covering 30, and the breeding house 20.

Furthermore, the air exchanging unit 41 has an intake pipe, an exhaust pipe, and two switch valves 44. The intake pipe and the exhaust pipe of the air exchanging unit 41 are connected to and communicate with the inner closed space of the breeding house 20 via the air covering 30. The switch valves 44 are respectively mounted on the intake pipe and the exhaust pipe of the air exchanging unit 41 in the outer closed space between the air covering 30 and the breeding house 20. The air exchanging unit 41 may control the flowing direction of the air into or out of the breeding house 20 and the air covering 30. Then, the relative air pressure among the outside environment 10, the air covering 30, and the breeding house 20 can be adjusted by the air exchanging unit 41 of the cleaning device 40. In addition, the air exchanging unit 41 of the cleaning device 40 may be used to control the temperatures and the concentrations of oxygen and carbon dioxide of the air covering 30 and the breeding house 20.

The sterilizing unit 42 is connected to the air exchanging unit 41 and communicates with the outside environment 10. Furthermore, the sterilizing unit 42 provides a sterilizing effect by a wet structure. The filtering units 43A, 43B are respectively mounted on the intake pipe and the exhaust pipe of the air exchanging unit 41 between the air covering 30 and the air exchanging unit 41. Furthermore, each one of the filtering units 43A, 43B has a filtering medium and a metal catalyst, the filtering medium is used to filter little molecule aerosols, and the metal catalyst is used to sterilize the air.

Figure 2:
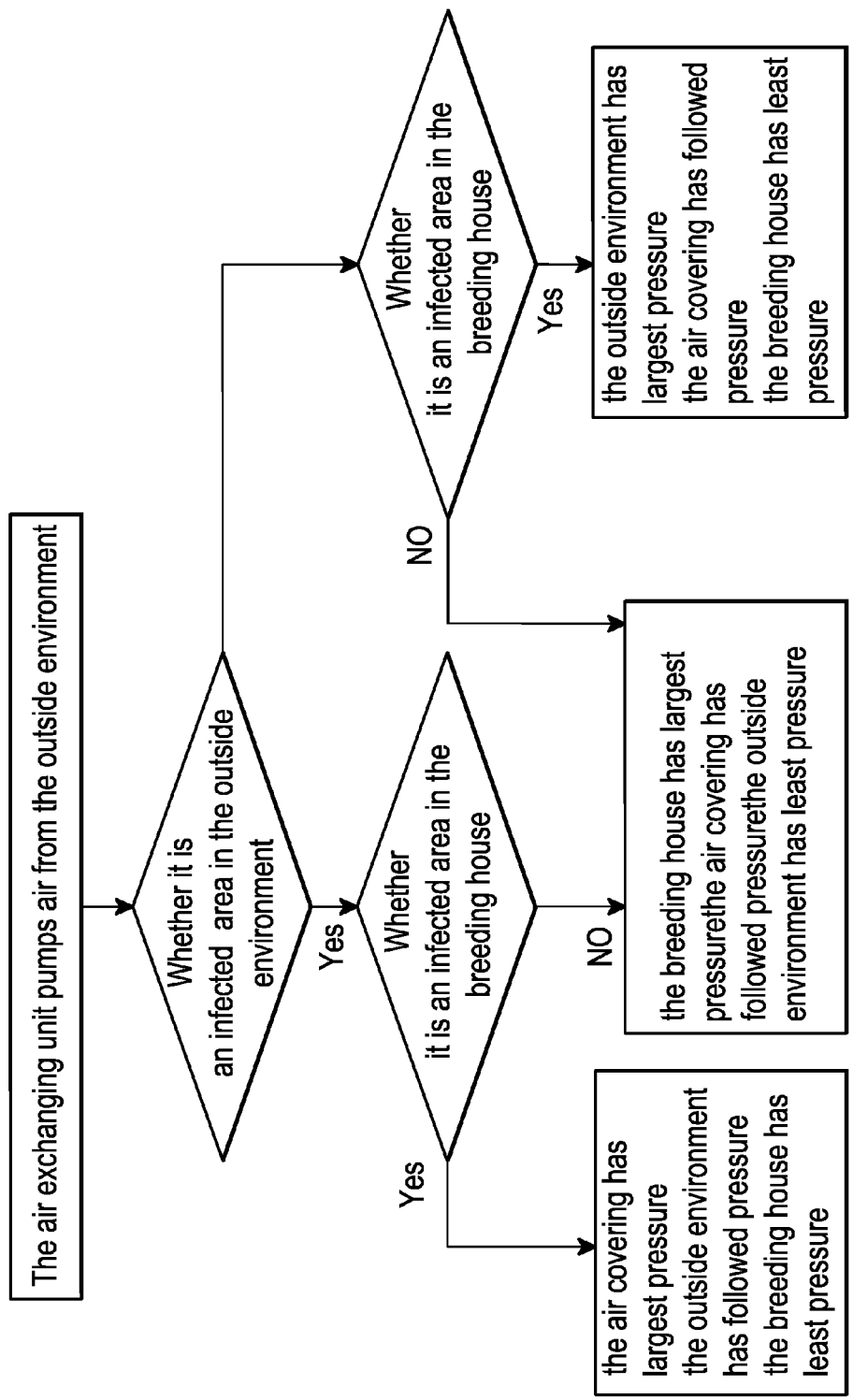
FIG. 2 is an operational block diagram of the environment cleaning system in FIG. 1.
Figure 3:
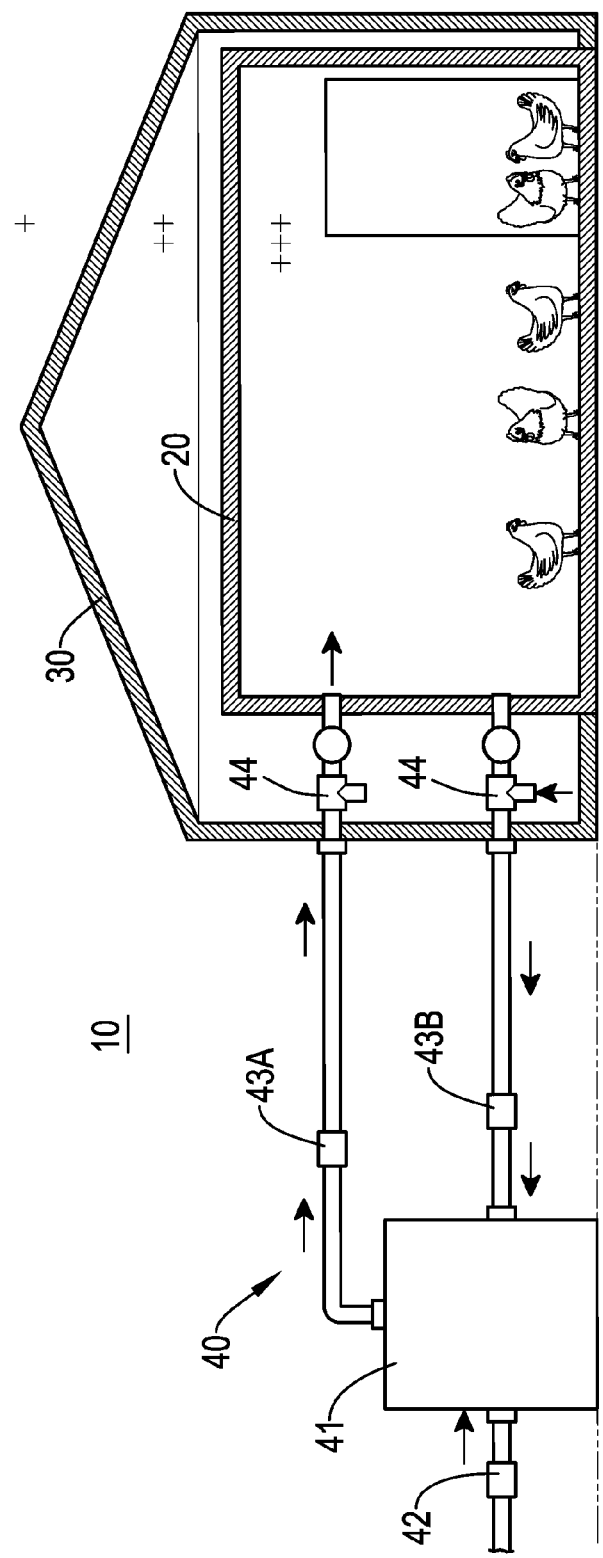
FIGS. 3 to 5 are operational side views of the environment cleaning system in FIG. 1 under different conditions.

With reference to FIGS. 2 and 3, when the outside environment 10 is an infected area or under a pollution condition, in order to prevent the animals in the breeding house 20 from getting sick by contamination of the outside environment 10, the air in the outside environment 10 cannot directly flow into the breeding house 20. The air in the outside environment 10 needs to be sterilized by the sterilizing unit 42 before flowing into the air exchanging unit 41. Then, the air after sterilization may be drawn into the breeding house 20 by controlling the switch valves 44.

In addition, when the air is flowing into the breeding house 20, the filtering unit 43A that is mounted on the intake pipe of the air exchanging unit 41 may sterilize the air again by the metal catalyst of the filtering unit 43A and may filter away the aerosols by the filtering medium of the filtering unit 43A. Additionally, the air in the outer closed space of the air covering 30 is drawn outwardly by the air exchanging unit 41 via the exhaust pipe. Then, the air pressure of the breeding house 20 is larger than the air pressure of the air covering 30, and the air pressure of the outside environment 10 is the lowest.

Consequently, the air in the breeding house 20 may naturally flow into the air covering 30 by the pressure relationship between the outside environment 10, the air covering 30, and the breeding house 20. Further, the air in the air covering 30 is flowed in the outside environment 10 by the air exchanging unit 41. Due to the relative pressure among the outside environment 10, the air covering 30, and the breeding house 20, the un-sterilized air in the outside environment 10 cannot directly flow into the air covering 30 and the breeding house 20, and this may provide an epidemic prevention effect to the animals in the breeding house 20.

Figure 4:
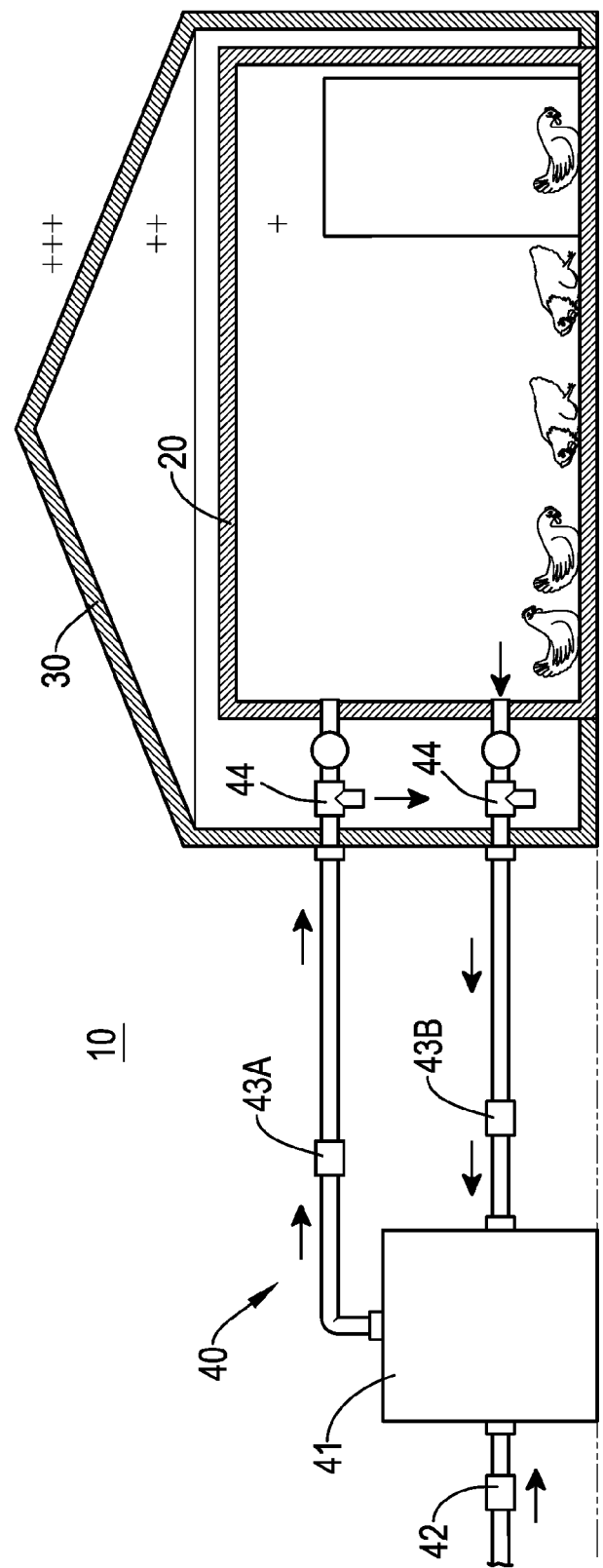

With reference to FIGS. 2 and 4, when the animals in the breeding house 20 get sick and the breeding house 20 becomes an infected area, if the air in the breeding house 20 flows without sterilization to the outside environment 10, the epidemic will spread. Therefore, the air of the outside environment 10 is pumped into the air exchanging unit 41 after the sterilizing unit 42 and flows into the outer closed space of the air covering 30 via the switch valve 44 on the intake pipe of the air exchanging unit 41. In addition, the air in the breeding house 20 is also pumped by the exchanging unit 41 via the exhaust pipe of the air changing unit 41, flows to the air exchanging unit 41 via the switch valve 44 on the exhaust pipe of the air exchanging unit 41, and is sterilized again by the metal catalyst of the filtering unit 43B, and the aerosols are filtered away by the filtering medium of the filtering unit 43B. Then, the air pressure of the outside environment 10 is larger than the air pressure of the air covering 30, and the air pressure of the breeding house 20 is the lowest.

Therefore, since the air pressure of the air covering 30 is larger than the air pressure of the breeding house 20, the air in the breeding house 20 cannot naturally flow into the air covering 30, and the air in the air covering 30 may naturally flow into the breeding house 20. The air in the breeding house 20 only can be drawn outwardly by the air exchanging unit 41. Consequently, when the breeding house 20 is an infected area, the pathogenic bacteria in the breeding house 20 cannot flow to the outside environment 10 by air convection, and this may prevent the epidemic from spreading to the outside environment 10.

Figure 5:
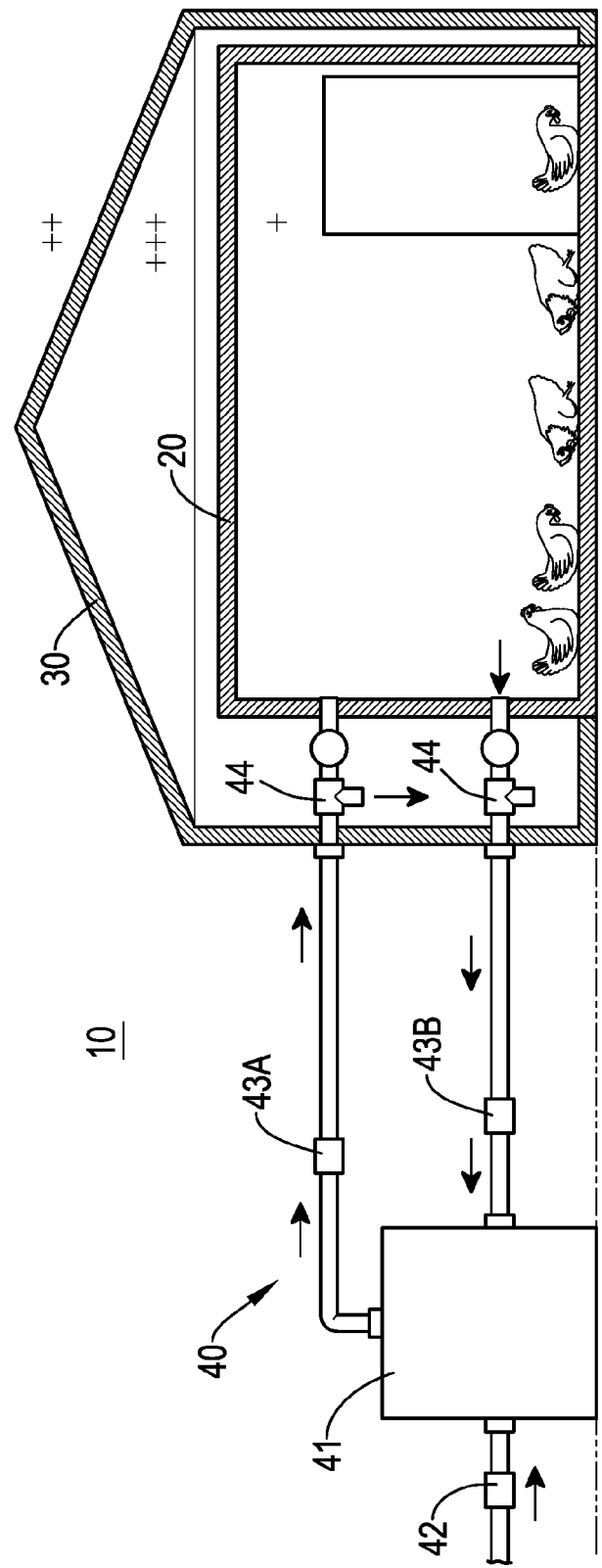

With reference to FIGS. 2 and 5, when the animals in the breeding house 20 get sick and other animals in the outside environment 10 also get sick, if the air in the breeding house 20 flows without sterilization to the outside environment 10, the other animals in the outside environment 10 may be cross-infected with the animals in the breeding house 20. The air in the outside environment 10 is pumped by the air exchanging unit 41, is sterilized by the sterilizing unit 42, and flows into the air covering 30 via the switch valve 44 that is mounted on the intake pipe of the air exchanging unit 41. Furthermore, the air in the breeding house 20 is also pumped by the air exchanging unit 41, and the filtering units 43A, 43B respectively sterilize and filter the airs in the outside environment 10 and the breeding house 20. Then, the air pressure of the air covering 30 is larger than the air pressure of the outside environment 10, and the air pressure of the breeding house 20 is the lowest.

Consequently, since the air pressure of the air covering 30 is larger than the air pressures of the breeding house 20 and the outside environment 10, the airs in the breeding house 20 and the outside environment 10 cannot naturally flow into the air covering 30. The airs in the breeding house 20 and the outside environment 10 only can be drawn by the air exchanging unit 41. Then, the air in the air covering 30 after sterilization may flow into the breeding house 20, and this may prevent the animals in the breeding house 20 from being cross-infected with the other animals in the outside environment 10.

Figure 6:
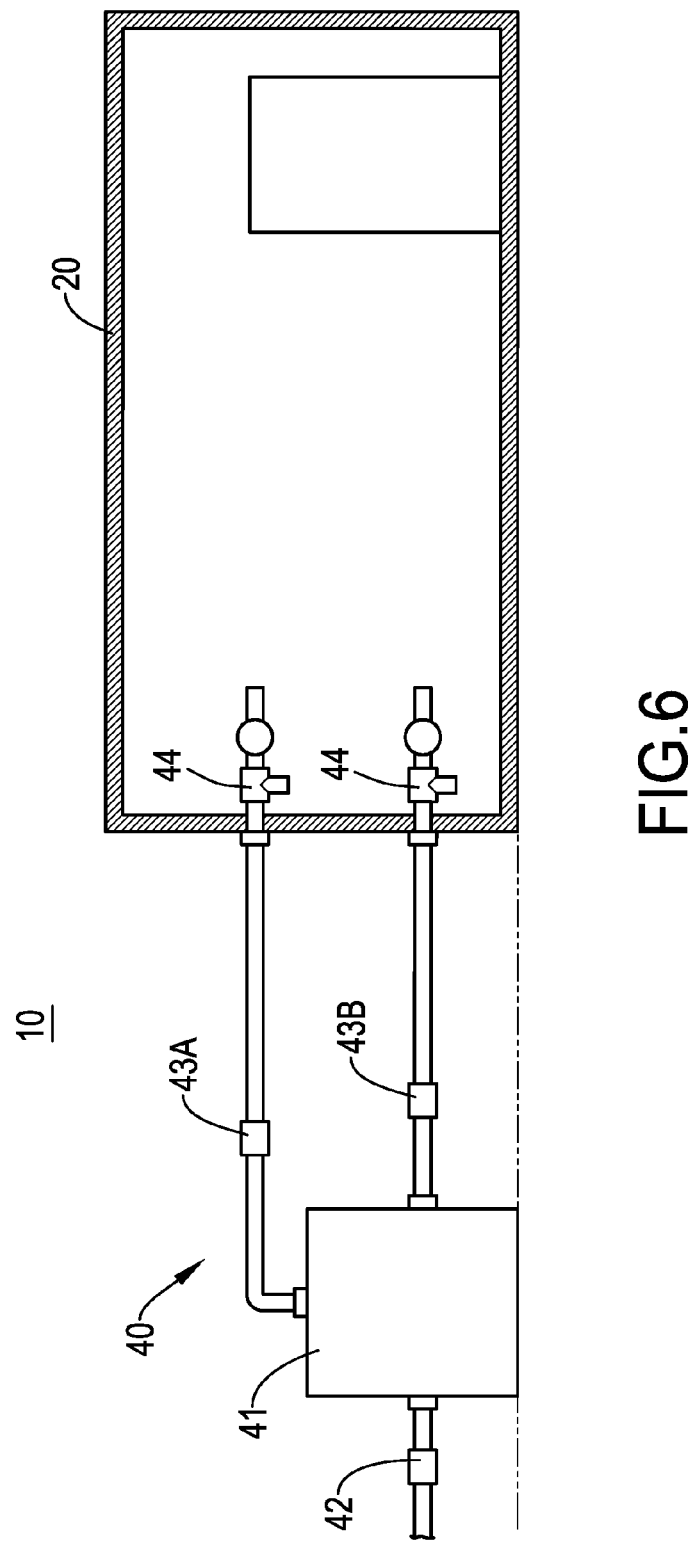
FIG. 6 is a side view in partial section of a second embodiment of an environment cleaning system for an animal breeding house in accordance with the present invention.

With reference to FIG. 6, a second embodiment of an environment cleaning system for an animal breeding house is substantially the same as the first embodiment except for the following features. The environment cleaning system of the second embodiment does not have the air covering 30, and the switch valves 44 of the cleaning system 40 are directly deposited in the inner closed space of the breeding house 20 to adjust the relative pressure between the breeding house 20 and the outside environment 10.

When the outside environment 10 is an infected area, the air in the outside environment 10 is pumped by the air exchanging unit 41 to be sterilized and filtered, and flows into the breeding house 20. In addition, the air in the breeding house 20 is also pumped by the air exchanging unit 41 to make the air pressure of the breeding house 20 larger than the air pressure of the outside environment 10, and this may prevent the un-sterilized air in the outside environment 10 from flowing into the breeding house 20.

When the breeding house 20 is an infected area, the air in the outside environment 10 is pumped by the air exchanging unit 41 to be sterilized and filtered, and flows into the breeding house 20. In addition, the air in the breeding house 20 is also pumped by the air exchanging unit 41 to make the air pressure of the breeding house 20 smaller than the air pressure of the outside environment 10, and this may prevent the un-sterilized air in the breeding house 20 from flowing into the outside environment 10.

Therefore, in the present invention, the air exchanging unit 41 is connected to the outside environment 10, the air covering 30, and the breeding house 20, and may control the relative pressure between the outside environment 10, the air covering 30, and the breeding house 20 to provide a unidirectional air flowing effect, and the flowing direction of the air is based on the relative pressure between the breeding house 20 and the air covering 30. Furthermore, the airs in the outside environment 10, the air covering 30, and the breeding house 20 only can be exchanged, sterilized, and filtered by the cleaning device 40, and this may provide an epidemic prevention effect to an animal breeding house.

According to the above-mentioned features and structural relationships, the environment cleaning system for an animal breeding house in accordance with the present invention has the following advantages.

1. The air exchanging unit 41 of the cleaning device 40 can pump air from the air covering 30 or the breeding house 20 according to the epidemic of the animals, to control the relative pressure between the breeding house 20, the air covering 30, and the outside environment 10 to provide a unidirectional air flowing effect and may provide an epidemic prevention effect to an animal breeding house.

2. When the outside environment 10 is an infected area, the air in the outside environment 10 is pumped by the air exchanging unit 41 to be sterilized and filtered, and flows into the breeding house 20. In addition, the air in the breeding house 20 is also pumped by the air exchanging unit 41 to make the air pressure of the breeding house 20 larger than the air pressure of the outside environment 10, and this may prevent the un-sterilized air in the outside environment 10 from flowing into the breeding house 20.

3. When the breeding house 20 is an infected area, the air in the outside environment 10 is pumped by the air exchanging unit 41 to be sterilized and filtered, and flows into the breeding house 20. In addition, the air in the breeding house 20 is also pumped by the air exchanging unit 41 to make the air pressure of the breeding house 20 smaller than the air pressure of the outside environment 10, and this may prevent the un-sterilized air in the breeding house 20 from flowing into the outside environment 10.

4. When the breeding house 20 and the outside environment 10 are infected areas at the same time, the air pressure of the air covering 30 is larger than the air pressure of the outside environment 10, and the air pressure of the breeding house 20 is the lowest. Then, the airs in the breeding house 20 and the outside environment 10 cannot naturally flow into the air covering 30. The airs in the breeding house 20 and the outside environment 10 only can be drawn by the air exchanging unit 41.

5. When the environment cleaning system does not have the air covering 30 and the outside environment 10 is an infected area, the cleaning device 40 may make the air pressure of the breeding house 20 larger than the air pressure of the outside environment 10. Furthermore, when the breeding house 20 is an infected area, the cleaning device 40 may make the air pressure of the breeding house 20 smaller than the air pressure of the outside environment 10.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An environment cleaning system for an animal breeding house having:
   an outside environment;
   a breeding house deposited in the outside environment and having an inner closed space;
   an air covering deposited in the outside environment, mounted over the entire breeding house, and having an outer closed space between the breeding house and the air covering; and
   a cleaning device deposited in the outside environment, connected to the air covering and the breeding house, and having
      an air exchanging unit deposited in the outside environment, connected to the air covering and the breeding house, and being used to exchange air among the outside environment, the air covering, and the breeding house; and
      at least one switch valve in the outer closed space connected to the air exchanging unit to control a relative pressure among the breeding house, the air covering, and the outside environment.

2. The environment cleaning system as claimed in claim 1, wherein the cleaning system has a sterilizing unit connected to the air exchanging unit and communicating with the outside environment to sterilize the air that is pumped from the outside environment by the air exchanging unit.

3. The environment cleaning system as claimed in claim 2, wherein the cleaning device has at least one filtering unit deposited between the air exchanging unit and the air covering.

4. The environment cleaning system as claimed in claim 3, wherein the air exchanging unit of the cleaning device is used to control the temperatures and the concentrations of oxygen and carbon dioxide of the air covering and the breeding house.

5. The environment cleaning system as claimed in claim 4, wherein
   air in the outside environment is pumped by the air exchanging unit, is sterilized by the sterilizing unit and flows into the breeding house;
   air in the air covering is pumped by the air exchanging unit and flows into the outside environment; and
   an air pressure of the breeding house is larger than an air pressure of the air covering, and the air pressure of the air covering is larger than an air pressure of the outside environment.

6. The environment cleaning system as claimed in claim 5, wherein each one of the at least one filtering unit has
   a filtering medium filtering the air that is pumped by the air exchanging unit from the outside environment and flows into the breeding house; and
   a metal catalyst sterilizing the air that is pumped by the air exchanging unit from the outside environment and flows into the breeding house.

7. The environment cleaning system as claimed in claim 4, wherein
   air in the outside environment is pumped by the air exchanging unit, is sterilized by the sterilizing unit and flows into the air covering;
   air in the breeding house is pumped by the air exchanging unit and flows into the outside environment; and
   an air pressure of the outside environment is larger than an air pressure of the air covering, and the air pressure of the air covering is larger than an air pressure of the breeding house.

8. The environment cleaning system as claimed in claim 7, wherein each one of the at least one filtering unit has
   a filtering medium filtering the air that is pumped by the air exchanging unit from the breeding house and flows into the outside environment; and
   a metal catalyst sterilizing the air that is pumped by the air exchanging unit from the breeding house and flows into the outside environment.

9. The environment cleaning system as claimed in claim 4, wherein air in the outside environment is pumped by the air exchanging unit, is sterilized by the sterilizing unit and flows into the air covering;

air in the breeding house is pumped by the air exchanging unit and flows into the outside environment; and an air pressure of the air covering is larger than an air pressure of the outside environment, and the air pressure of the outside environment is larger than an air pressure of the breeding house.

10. The environment cleaning system as claimed in claim 9, wherein each one of the at least one filtering unit has a filtering medium filtering the air that is pumped by the air exchanging unit from the breeding house and flows into the outside environment; and a metal catalyst sterilizing the air that is pumped by the air exchanging unit from the breeding house and flows into the outside environment.

11. The environment cleaning system as claimed in claim 3, wherein air in the outside environment is pumped by the air exchanging unit, is sterilized by the sterilizing unit and flows into the breeding house;

air in the air covering is pumped by the air exchanging unit and flows into the outside environment; and an air pressure of the breeding house is larger than an air pressure of the air covering, and the air pressure of the air covering is larger than an air pressure of the outside environment.

12. The environment cleaning system as claimed in claim 11, wherein each one of the at least one filtering unit has a filtering medium filtering the air that is pumped by the air exchanging unit from the outside environment and flows into the breeding house; and a metal catalyst sterilizing the air that is pumped by the air exchanging unit from the outside environment and flows into the breeding house.

13. The environment cleaning system as claimed in claim 3, wherein air in the outside environment is pumped by the air exchanging unit, is sterilized by the sterilizing unit and flows into the air covering;

air in the breeding house is pumped by the air exchanging unit and flows into the outside environment; and an air pressure of the outside environment is larger than an air pressure of the air covering, and the air pressure of the air covering is larger than an air pressure of the breeding house.

14. The environment cleaning system as claimed in claim 13, wherein each one of the at least one filtering unit has a filtering medium filtering the air that is pumped by the air exchanging unit from the breeding house and flows into the outside environment; and a metal catalyst sterilizing the air that is pumped by the air exchanging unit from the breeding house and flows into the outside environment.

15. The environment cleaning system as claimed in claim 3, wherein air in the outside environment is pumped by the air exchanging unit, is sterilized by the sterilizing unit and flows into the air covering;

air in the breeding house is pumped by the air exchanging unit and flows into the outside environment; and an air pressure of the air covering is larger than an air pressure of the outside environment, and the air pressure of the outside environment is larger than an air pressure of the breeding house.

16. The environment cleaning system as claimed in claim 15, wherein each one of the at least one filtering unit has a filtering medium filtering the air that is pumped by the air exchanging unit from the breeding house and flows into the outside environment; and a metal catalyst sterilizing the air that is pumped by the air exchanging unit from the breeding house and flows into the outside environment.

* * * * *